United States Patent [19]

Schulman et al.

[11] 4,223,679
[45] Sep. 23, 1980

[54] TELEMETRY MEANS FOR TISSUE STIMULATOR SYSTEM

[75] Inventors: Joseph H. Schulman, Los Angeles; Brian M. Mann, Northridge; Russell R. Beane, Sepulveda, all of Calif.

[73] Assignee: Pacesetter Systems, Inc., Sylmar, Calif.

[21] Appl. No.: 16,272

[22] Filed: Feb. 28, 1979

[51] Int. Cl.³ .............................................. A61N 1/36
[52] U.S. Cl. ............................................. 128/419 PT
[58] Field of Search .................. 128/419 PS, 419 PT, 128/697

[56] References Cited

U.S. PATENT DOCUMENTS

| | | | |
|---|---|---|---|
| 3,135,264 | 6/1964 | Tischler et al. | 128/697 |
| 3,195,540 | 7/1965 | Waller | 128/419 PT |
| 3,777,762 | 12/1973 | Nielsen | 128/419 PT |
| 3,830,242 | 8/1974 | Greatbatch | 128/419 PT |
| 3,942,535 | 3/1976 | Schulman | 128/419 PS |
| 4,026,305 | 5/1977 | Brownlee et al. | 128/419 PT |
| 4,142,533 | 3/1979 | Brownlee et al. | 128/419 PT |

Primary Examiner—William E. Kamm
Attorney, Agent, or Firm—Freilich, Hornbaker, Wasserman, Rosen & Fernandez

[57] ABSTRACT

A telemetry system for use in a living tissue stimulator system in which an externally located oscillator is controlled by impedance changes in an impedance reflecting circuit located in an implantable tissue stimulator. In a first embodiment the impedance reflecting circuit is an LC circuit thereby frequency modulating the externally located oscillator and in a second embodiment it is an LR circuit thereby amplitude modulating the externally located oscillator. More specifically, the externally located oscillator drives an LC circuit in which the inductor is positioned in magnetically coupled relationship to an inductor in the impedance reflecting circuit. The externally located oscillator is chosen so that its frequency and amplitude is partially determined by the impedance of the LC circuit and the magnetically coupled impedance reflecting circuit. A parameter or signal to be telemetered, which could be in the form of a digital or an analog signal, is used to modulate an output frequency of a voltage controlled oscillator located in the implantable tissue stimulator. This frequency modulated output of the voltage controlled oscillator drives an FET switch which alters the impedance of the impedance reflecting circuit, thereby modulating the output of the externally located oscillator. Thus, a telemetry system is provided in which minimum power is required from the implantable tissue stimulator.

32 Claims, 5 Drawing Figures

TELEMETRY MEANS FOR TISSUE STIMULATOR SYSTEM

FIELD OF THE INVENTION

The invention relates to telemetry systems for implantable tissue stimulators such as heart pacemakers.

BACKGROUND OF THE INVENTION

Recent developments in implantable pacemakers have included providing a memory means in the pacemaker for controlling characteristics of a tissue stimulation pulse. In order to enhance flexibility of such programmable pacemakers, means have been developed to transmit parameters or control signals to be stored within the pacemaker memory means and verify control signals stored within the memory means as well as other parameters such as voltage, temperature, etc., transmitted from the pacemaker. Conventional means for transmitting signals from the pacemaker to an external receiving means have typically utilized some sort of amplitude modulation scheme, although it has long been known in the communications art that frequency modulation is less susceptible to noise than amplitude modulation. However, FM/FM or FM/AM systems have not been widely utilized in implantable tissue stimulators because of the power required to generate and transmit these types of telemetry signals. The present invention provides both an FM/FM and FM/AM telemetry system for a living tissue stimulator system which greatly reduces power required from an implanted power source.

SUMMARY OF THE INVENTION

The invention provides a telemetry system for a living tissue stimulator system comprising an implantable tissue stimulator and an external receiving means. The external receiving means includes a first oscillator whose frequency is partially determined by a first inductor also located in the external receiving means. An impedance reflecting circuit including a second inductor which is in magnetically coupled relationship to the first inductor is located within the implantable tissue stimulator. A voltage controlled oscillator is also provided which has an output frequency related to a signal to be telemetered. A control means is provided for controlling the impedance of the impedance reflecting circuit in relation to the voltage controlled oscillator output voltage. This impedance being magnetically coupled to the first oscillator through the first inductor causes a shift in the first oscillator frequency if the coupled impedance is reactive or a change on the first oscillator amplitude if the coupled impedance is resistive, thereby creating an FM/FM or FM/AM telemetry signal without having to power a transmitting means in the implantable human tissue stimulator. In a specific embodiment, the first oscillator has a nominal output frequency of 30KHz. The voltage controlled oscillator 16 has a frequency which varies between 1.0 and 2.5 KHz.

DETAILED DESCRIPTION

As required, detailed illustrative embodiments of the invention are disclosed herein. These embodiments exemplify the invention and are currently considered to be the best embodiments for such purposes. However, it is to be recognized that the specific embodiments disclosed are representative in providing a basis for the claims which define the scope of the present invention.

As previously explained, the invention provides an FM/FM or FM/AM telemetry system for a living tissue stimulator system comprising in implantable living tissue stimulator and an external receiving means. An impedance reflecting circuit is provided within the implantable tissue stimulator, an inductor of the impedance reflecting circuit being magnetically coupled to an inductor which is connected to an oscillator within the external receiving means. A voltage controlled oscillator is connected to an FET switch in the impedance reflecting circuit, the frequency of the voltage controlled oscillator being determined by the voltage of a signal to be telemetered. The output voltage of the voltage controlled oscillator biases the FET switch so that the impedance of the impedance reflecting circuit is altered, thereby altering the impedance seen by the oscillator in the external receiving means. If this altered impedance is reactive, it results in frequency shifts in the externally located oscillator whose output thus comprises an FM/FM modulated telemetry signal generated without having to power an active transmission means in the implantable tissue stimulator. If the altered impedance is resistive, then amplitude changes will occur in the externally located oscillator output, this output then comprising an FM/AM modulated telemetry signal.

Figure 1:
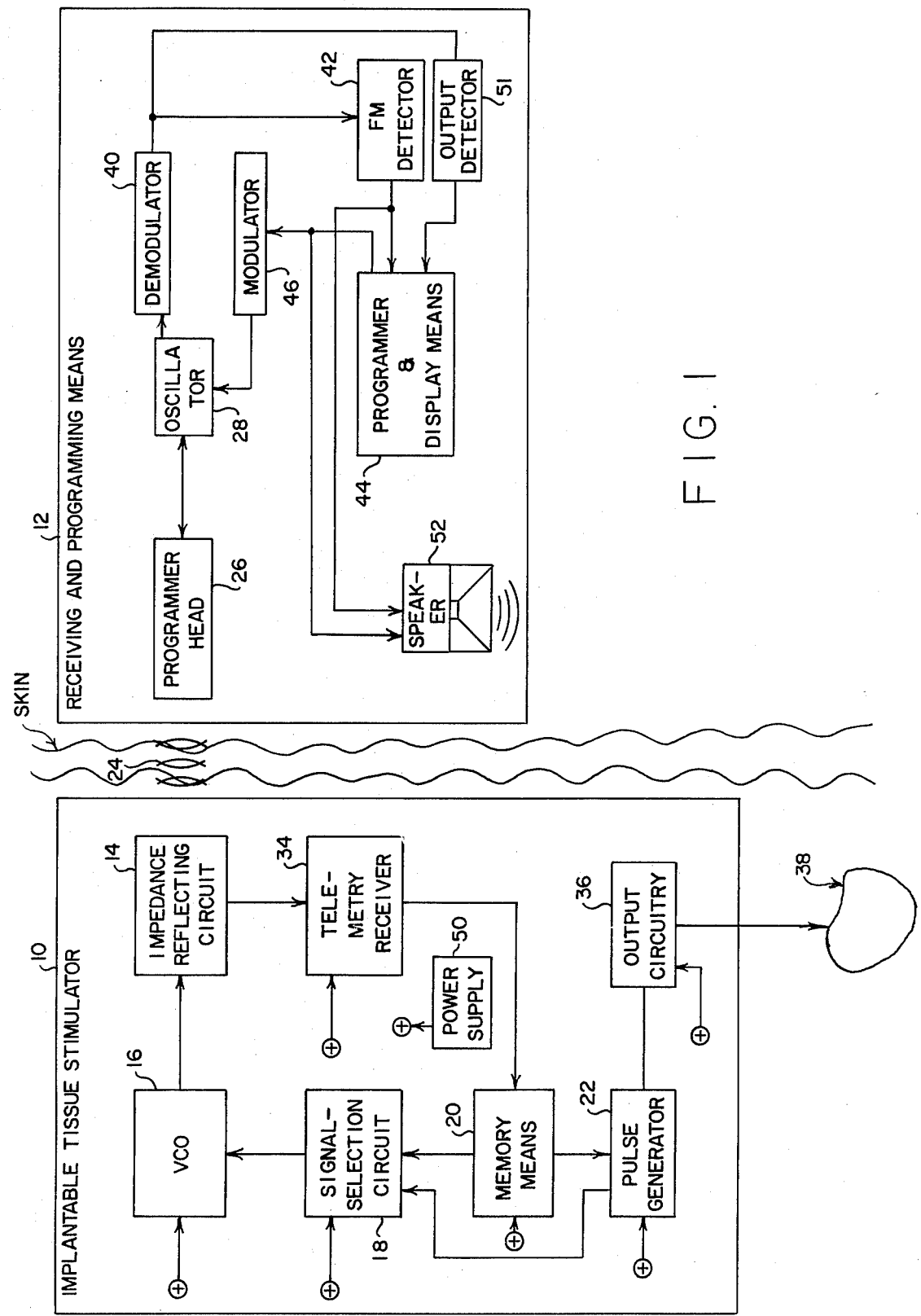
FIG. 1 is a block diagram of a human tissue stimulator system incorporating the telemetry system provided by the invention.

Referring to FIG. 1, a living tissue stimulator system comprises an implantable tissue stimulator 10 and a receiving and programming means 12. The implantable tissue stimulator 10 could be a device generally known as a heart pacemaker or an implantable drug dispenser. An impedance reflecting circuit 14 is provided, the impedance being related to an output voltage from a voltage controlled oscillator (VCO) 16 whose frequency is determined by an input signal to be telemetered. A signal selection circuit 18 receives input voltages from both a memory means 20 which provides digital inputs, and a pulse generator 22 which provides analog inputs. The signal selection circuit 18 includes means for selecting one of its input signals to be telemetered in accordance with control signals from the memory means 20, the selected signal frequency-modulating the VCO 16. The frequency modulated VCO 16 output then alters, as will be explained below, the impedance of the impedance reflecting circuit 14 which is magnetically coupled as schematically represented at 24 to a programmer head 26 which in turn is coupled to an oscillator 28. The output of the oscillator 28 is determined by the combined impedance of the programmer head 26 and the impedance reflecting circuit 14 as coupled to the programmer head 26. Thus the oscillator 28 output is an FM modulated signal if the coupled impedance is reactive and an AM modulated signal if the coupled impedance is resistive. In both cases the FM or AM modulation on the oscillator 28 output is related to the output of the VCO 16 which is FM modulated by the signal to be telemetered.

The implantable tissue stimulator 10 also includes a telemetry receiver 34 for receiving signals from the receiving and programming means 12 and output circuitry 36 which supplies stimulating pulses to a heart 38. The output of the oscillator 28 in the receiving and programming means 12 is provided to a demodulator 40, the output of which corresponds to the output of the implantable tissue stimulator VCO 16. This output is then provided to an FM detector 42 which in turn provides an output signal to a programmer and display means 44 which is proportional to the signal to be telemetered provided by the signal selection circuit 18. In addition, the programmer and display means 44 provides control signals to be telemetered to the implantable tissue stimulator 10 to a modulator 46 which modulates the oscillator 28. The output of the oscillator 28 is magnetically coupled through the programmer head 26 to the impedance reflecting circuit 14 whose output is provided to the telemetry receiver 34. In addition, the implantable tissue stimulator 10 is powered by a power supply 50 which could be a battery.

An output detector 51 generates a position head signal whose presence indicates that insufficient magnetic coupling exists between the programmer head 26 and the impedance reflecting circuit 14. The output detector will be described in detail below.

In addition a speaker system 52 is provided. The speaker system 52 contains first and second audio oscillators which are responsive to signals going to the modulator 46 and signals from the FM detector 42 respectively. Thus, a first audio signal having a frequency corresponding to that of the first audio oscillator is provided when data is being transmitted to the implantable tissue stimulator 10 and a second audio signal having a frequency corresponding to that of the second audio oscillator when data from the implantable tissue stimulator 10 is received. This audio signal can be used by an operator to immediately determine the presence of received or transmitted telemetry signals.

Figure 2:
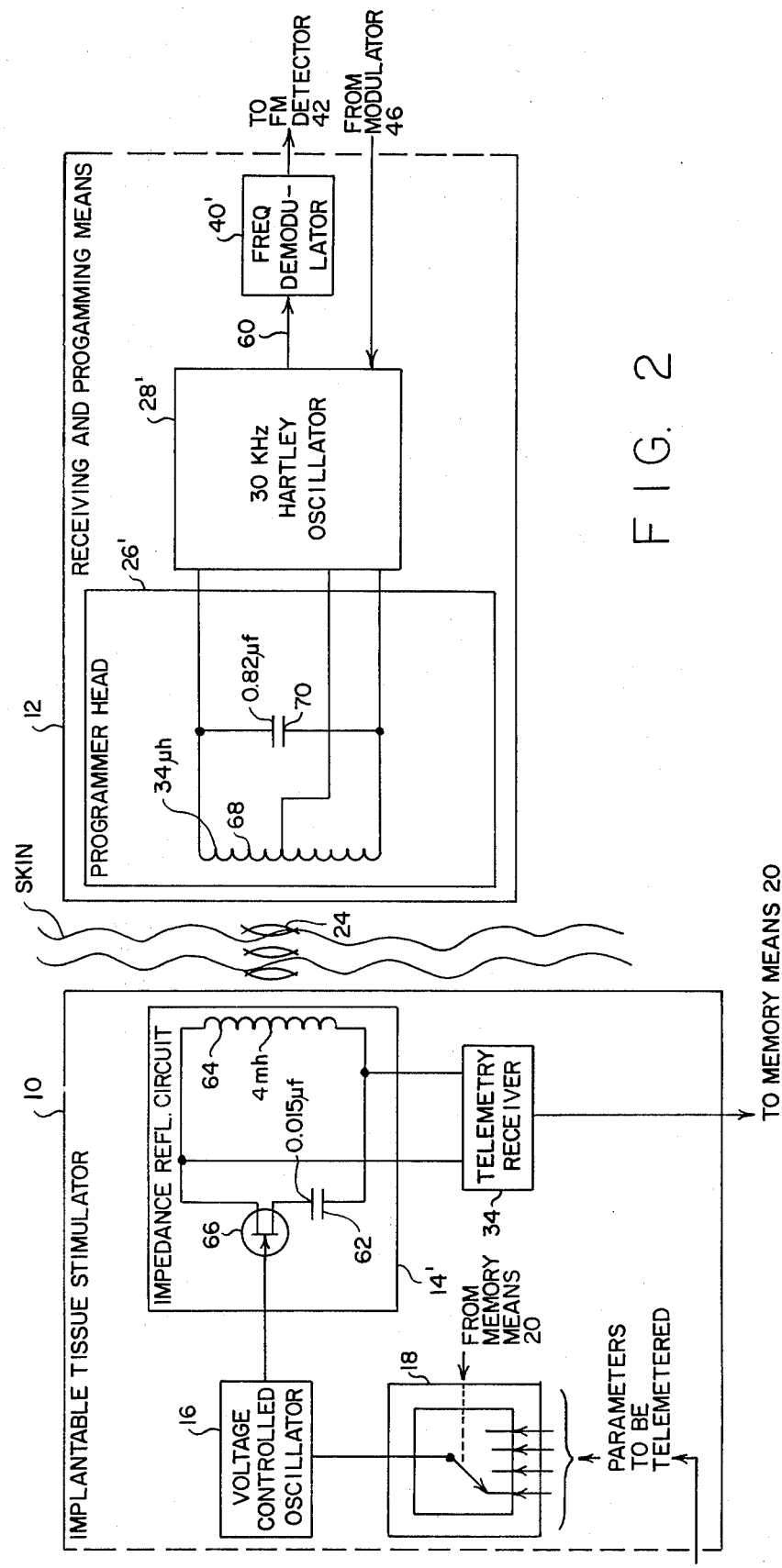
FIG. 2 is a block and schematic diagram showing a FM/FM telemetry system provided by the invention.

In an FM/FM embodiment of the invention shown in FIG. 2, a 30 KHz Hartley oscillator 28 is utilized. Impedance changes in an impedance reflecting circuit 14' produce approximately a 2Hz shift in the oscillator 28 output frequency. For diagramatic purposes, the oscillator 28 is defined as not including its associated tank circuit, the tank circuit being contained in the programmer head 26. The impedance reflecting circuit 14' comprises a 0.015 microfarad capacitor 62 and a 4 millihenry inductor 64, the inductor 64 and capacitor 62 combination being connected in series through an FET switch 66. The programmer head 26' contains a 34 microhenry inductor 68 and a 0.82 microfarad capacitor 70, the inductor 68 and capacitor 70 being connected in parallel to the oscillator 28'. Thus the programmer head inductor 68 capacitor 70 combination comprises a first LC circuit or tank circuit which is magnetically coupled to a second LC circuit comprising the capacitor 62 and inductor 64. For optimum FM detection, the LC circuit in the impedance reflecting circuit 14' should be detuned with respect to the impedance reflecting LC circuit in the programmer head 26'. The FET switch 66 varies the impedance of the impedance reflecting circuit 14' in accordance with the output voltage of the VCO 16, the frequency of which is controlled by a signal to be telemetered from the signal selection circuit 18 as previously explained. In this embodiment, the VCO 16 is chosen so that a digital 0 corresponds to 2.1 KHz plus or minus 10% and a logical 1 corresponds to 1.2 KHz plus or minus 20%. For analog signals to be telemetered, the VCO 16 is chosen so that its output frequency is between 1000 Hz and 2.5 KHz. The output from the oscillator 28' is then demodulated by frequency demodulator 40', its output then corresponding to the output signal from the VCO 16 as previously explained.

Figure 3:
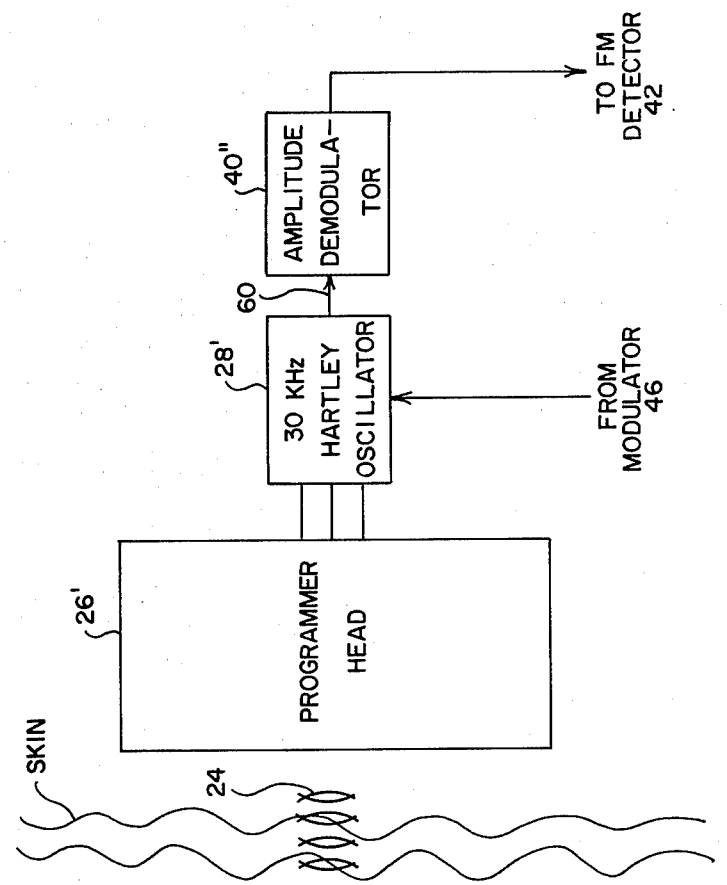
FIG. 3 is a block and schematic diagram showing an FM/AM telemetry system provided by the invention.
Figure 3:
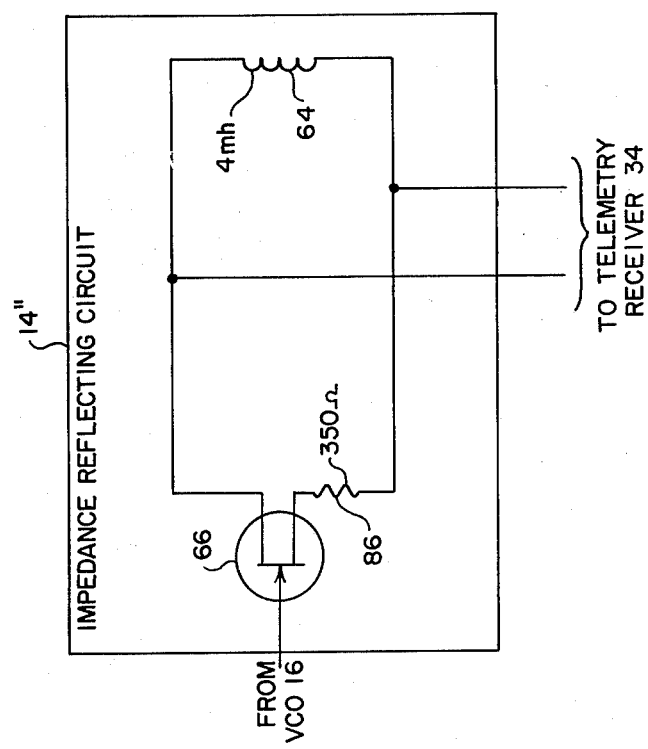

In an FM/AM embodiment of the invention shown in FIG. 3, the same 30 KHz Hartley oscillator 28' is utilized. However, the impedance reflecting circuit 14" comprises the 4 millihenry inductor 64 and a 350 ohm resistor 86, the inductor 64 and resistor 86 combination being connected in series through the FET switch 66. As in the FM/FM embodiment, the programmer head 26' comprises a first LC circuit which is magnetically coupled to the LR impedance reflecting circuit 14" comprising the inductor 64 and resistor 86. The FET switch 66 varies the impedance of the impedance reflecting circuit 14" in accordance with the output of the VCO 16, the frequency of which is controlled by a signal to be telemetered from the signal selection circuit as previously explained. However, in this embodiment, the impedance coupled to the programmer head 26α is largely resistive, thereby resulting in an amplitude modulation of the oscillator 28' output signal appearing on line 60. Thus an amplitude demodulator 40" is utilized to provide an output signal related to the VCO 16 output signal. The remainder of the FM/AM telemetry system is the same as the FM/FM telemetry system.

Figure 4A:
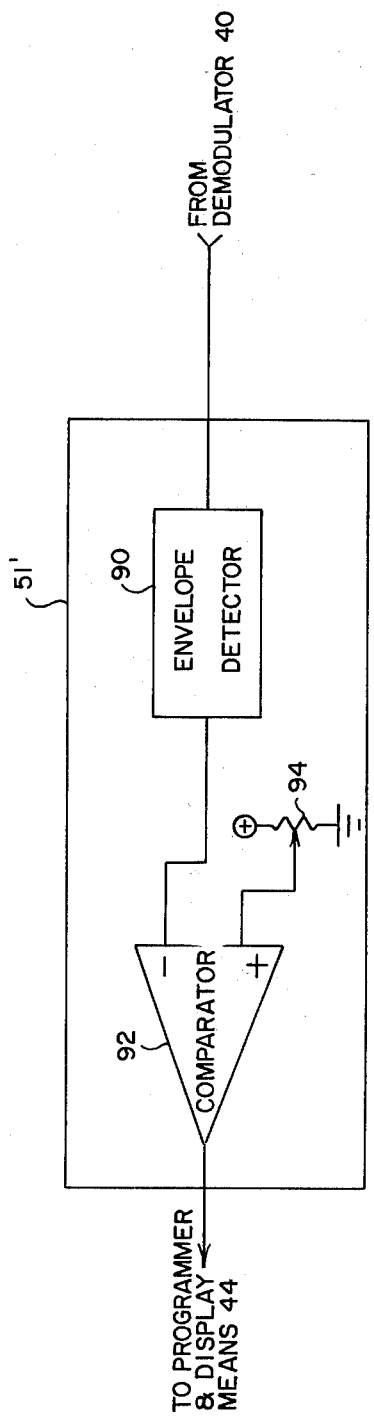
FIGS. 4A and 4B are block and schematic diagrams showing demodulator output detectors.
Figure 4B:
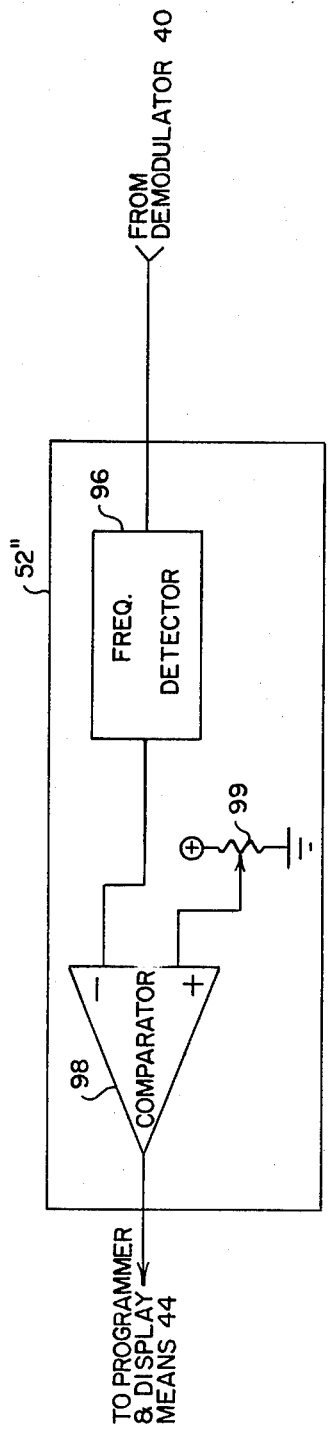

As previously explained, the purpose of the output detector 51 is to generate a position head signal which indicates that sufficient magnetic coupling does not exist between the programmer head 26 and the impedance reflecting circuit 14. This position head signal can be displayed, thereby informing an operator that the programmer head should be repositioned with respect to the tissue stimulator 10. A first output detector 51' is shown in FIG. 4A. It comprises an envelope detector 90 which provides an output voltage proportional to the amplitude of the demodulator 40 output. As previously explained, the amplitude of the demodulator 40 output corresponds to the degree of coupling between the programmer head 26 and the impedance reflecting circuit 14. Thus if there is insufficient magnetic coupling, the demodulator 40 output will be low. A comparator 92 is provided which compares the output of the envelope detector 90 with a predetermined voltage derived from a potentiometer 94. If the output of the envelope detector 90 is above the predetermined voltage for the potentiometer 94, the comparator provides a first output voltage; if below, the comparator 92 provides a second output voltage. The presence of the second output voltage indicates that the programmer head 26 should be repositioned. Another output detector 52" is shown in FIG. 4B. This detector comprises a frequency detector 96 which provides an output voltage related to the frequency of the VCO 16. Thus, if there is insufficient magnetic coupling, there will be no demodulator 40 output signal related to the VCO 16 output signal and, therefore, no frequency to be detected. A comparator 98 is provided which compares the output of the frequency detector 96 with a predetermined voltage derived from a potentiometer 99. The predetermined voltage could be set to correspond to a frequency of 1000 Hz from the frequency detector 96 because the VCO 16 frequency never gets that low as previously explained. If the output of the frequency detector 96 is above the predetermined voltage from the potentiometer 97, the comparator 98 provides a first output voltage; if below, the comparator provides a second output voltage. The presence of the second output voltage indicates that the programmer head 26 should be repositioned.

Thus, as one can appreciate, a telemetry system provided by the present invention incorporates an impedance reflecting circuit in an implantable tissue stimulator whose impedance varies as a function of a frequency modulated signal. Although in the above-described embodiments an FET switch 66 has been utilized for varying the impedance of the impedance reflecting circuit 14, it should be understood that other types of impedance varying devices such as transistor switches, variable resistors and the like could also be utilized. In addition, although the impedance reflecting circuit 14 disclosed comprises an LC circuit or a LR circuit, other configurations could be utilized. For example, the LC circuit could have a second capacitor in parallel with the inductor 64. Also, it should be recognized that the impedance seen by the oscillator 28 could be divided in many ways between the programmer head 26 and the impedance reflecting circuit 14, the only requirement being that alteration of the impedance of the impedance reflecting circuit is sufficient for the output of the oscillator 28 to have a desired frequency shift or amplitude variation.

It should now be apparent from the above description, that a telemetry means for a living tissue stimulator system has been disclosed in which the frequency or amplitude of an oscillator in an externally located receiving means is varied by a variable impedance located within an implantable tissue stimulator, the impedance being varied in accordance with a frequency modulated output from a voltage controlled oscillator whose frequency is controlled by digital and analog parameters to be telemetered.

What is claimed is:

1. In a living tissue stimulator system comprising an implantable tissue stimulator and an external receiving means, a telemetry means comprising:
a first oscillator means;
a first LC circuit coupled to said first oscillator means;
an impedance reflecting circuit in magnetically coupled relationship to said first LC circuit whereby the combined impedance of said first LC circuit and said impedance reflecting circuit combination is related to the impedance of said impedance reflecting circuit;
altering means for varying the impedance of said impedance reflecting circuit;
a second oscillator means having an output frequency related to a signal voltage to be telemetered; and
means for controlling said altering means by said second oscillator means whereby characteristics of an output signal from said first oscillator means are related to the impedance of said impedance reflecting circuit.

2. The telemetry means of claim 1 in which said first LC circuit is located in said external receiving means and said impedance reflecting circuit is located in said implantable tissue stimulator.

3. The telemetry means of claim 2 wherein said impedance reflecting circuit comprises an LC circuit thereby resulting in the frequency of said first oscillator output signal being related to the impedance of said impedance reflecting circuit.

4. The telemetry means of claim 2 wherein said impedance reflecting circuit comprises an LR circuit thereby resulting in the amplitude of said first oscillator output signal being related to the impedance of said impedance reflecting circuit.

5. The telemetry means of claim 2 further comprising:
means for demodulating said first oscillator output signal; and
means for determining the amplitude of said demodulated oscillator output signal, thereby providing a signal related to the magnetic coupling between said first LC circuit and said impedance reflecting circuit.

6. The telemetry means of claim 5 further comprising comparing means for providing a first output signal when said demodulated signal amplitude is above a predetermined level and a second output signal when said demodulated signal amplitude is below said predetermined level, said second output signal indicating that said first LC circuit should be closer to said impedance reflecting circuit in order to increase their magnetic coupling.

7. The telemetry means of claim 5 wherein said impedance reflecting circuit comprises an LC circuit and said means for demodulating comprises a frequency demodulator.

8. The telemetry means of claim 5 wherein said impedance reflecting circuit comprises an LR circuit and said means for demodulating comprises an amplitude demodulator.

9. The telemetry means of claim 2 further comprising:
means for demodulating said first oscillator output signal; and
means for providing a first output signal when said demodulated oscillator output signal frequency is above a predetermined frequency and a second output signal when said demodulated oscillator output signal frequency is below said predetermined frequency, said second output signal indicating insufficient magnetic coupling between said first LC circuit and said impedance reflecting circuit.

10. The telemetry means of claim 1 in which said altering means comprises an FET switch.

11. The telemetry means of claim 1 further comprising means for generating a recovered voltage from said first oscillator means, the recovered voltage being related to said signal voltage to be telemetered.

12. The telemetry means of claim 11 further comprising means for providing an audio signal related to said recovered voltage.

13. In combination with a living tissue stimulator system comprising an implantable tissue stimulator and an external receiving means, a telemetry system comprising:
a first oscillator located in said external receiving means;
an impedance creating circuit comprising a first inductor coupled to said first oscillator and partially determinative of said first oscillator signal characteristics;
an impedance reflecting circuit comprising a second inductor in magnetically coupled relationship to said first inductor and located in said implantable tissue stimulator;

a voltage controlled oscillator having an output frequency related to a signal to be telemetered; and control means for altering impedance characteristics of said impedance reflecting circuit in relation to said voltage controlled oscillator output voltage, thereby altering said first oscillator signal characteristics.

14. The telemetry system of claim 13 in which said control means comprises a variable impedance incorporated in said impedance reflecting circuit.

15. The telemetry system of claim 14 in which said variable impedance is an FET swtich.

16. The telemetry system of claim 13 further comprising means to develop a signal proportional to said signal to be telemetered from said first oscillator output signal characteristics.

17. In combination with a living tissue stimulator system comprising an implantable tissue stimulator and an external receiving means, an FM/FM telemetry system comprising:

a first oscillator located in said external receiving means;

an impedance creating circuit comprising a first inductor coupled to said first oscillator and partially determinative of said first oscillator frequency;

an impedance reflecting circuit comprising a capacitor and a second inductor in magnetically coupled relationship to said first inductor and located in said implantable tissue stimulator;

a voltage controlled oscillator having an output frequency related to a signal to be telemetered; and control means for altering impedance characteristics of said impedance reflecting circuit in relation to said voltage controlled oscillator output voltage, thereby altering the output signal frequency of said first oscillator.

18. The FM/FM telemetry system of claim 17 wherein said control means comprises an FET switch.

19. The FM/FM telemetry system of claim 17 further comprising:

an FM demodulator for demodulating said oscillator output signal; and an FM detector for providing an output voltage related to the frequency of said demodulated oscillator output signal, said FM detector output signal being related to said signal to be telemetered.

20. The FM/FM telemetry system of claim 19 further comprising comparing means for providing a first output signal when said demodulated oscillator output signal is above a predetermined amplitude level, and a second output signal when said demodulated signal amplitude is below said predetermined level, said second output signal indicating that said first inductor should be repositioned with respect to said second inductor.

21. In combination with a living tissue stimulator system comprising an implantable tissue stimulator and an external receiving means, an FM/AM telemetry system comprising:

a first oscillator located in said external receiving means;

an impedance creating circuit comprising a first inductor coupled to said first oscillator;

an impedance reflecting circuit comprising a resistor and a second inductor in magnetically coupled relationship to said first inductor and located in said implantable tissue stimulator;

a voltage controlled oscillator having an output frequency related to a signal to be telemetered; and control means for altering impedance characteristics of said impedance reflecting circuit in relation to said voltage controlled oscillator output voltage, thereby altering the output signal amplitude of said first oscillator.

22. The FM/AM telemetry system of claim 21 wherein said control means comprises an FET swtich.

23. The FM/AM telemetry system of claim 21 further comprising:

an amplitude demodulator for demodulating said oscillator output signal; and an FM detector for providing an output voltage related to the frequency of said demodulated oscillator output signal, said FM detector output signal being related to said signal to be telemetered.

24. The FM/AM telemetry system of claim 23 further comprising means for providing a first output signal when said demodulated oscillator output signal frequency is above a predetermined value and a second output signal when said demodulated oscillator output signal frequency is below said predetermined value, said second output signal indicating that said first inductor should be repositioned with respect to said second conductor.

25. A method for telemetering information from an implantable living tissue stimulator to a receiving means, the steps comprising:

varying the frequency of a voltage controlled oscillator in said implantable living tissue stimulator in relation to a signal to be telemetered;

altering the impedance of an impedance reflecting circuit comprising a first inductor in relation to said voltage controlled oscillator output voltage;

magnetically coupling said first inductor to a second inductor coupled to an external oscillator located in said receiving means whereby an output signal of said external oscillator is related to the impedance of said impedance reflecting circuit.

26. The method of claim 25 further comprising the step of using said external oscillator output signal to develop a signal related to said signal to be telemetered.

27. The method of claim 26 further comprising the step of providing a signal indicating that said first inductor is not sufficiently magnetically coupled to said second inductor.

28. In combination with an implantable device for humans having an impedance reflecting circuit and an external receiving means, a telemetry system comprising:

means for altering the impedance of said impedance reflecting circuit in relation to a signal to be telemetered from said device, said impedance reflecting circuit comprising a first inductor;

a second inductor in magnetically coupled relationship to said first inductor; and said external receiving means comprises impedance sensing means connected to said second inductor for providing an output signal responsive to impedance changes in said impedance reflecting circuit, said output signal being related to said signal to be telemetered.

29. The telemetry system of claim 28 wherein said means for altering is located in said implantable device for humans.

30. The telemetry system of claim 28 wherein said means for altering comprises:

a voltage controlled oscillator having an output signal related to said signal to be telemetered; and variable impedance means coupled to said first inductor, said variable impedance means being responsive to said voltage controlled oscillator output signal.

31. The telemetry system of claim 30 wherein said variable impedance means comprises an FET switch.

32. The telemetry system of claim 30 wherein said impedance sensing means comprises an external oscillator coupled to said second inductor whereby an output signal from said external oscillator is related to the impedance of said impedance reflecting circuit.

* * * * *